United States Patent
Kenndoff

(10) Patent No.: US 9,681,934 B2
(45) Date of Patent: Jun. 20, 2017

(54) USE OF A SEMI-OCCLUSIVE FLEXIBLE FLAT WOUND DRESSING FOR TREATING WOUNDS IN ANIMALS

(75) Inventor: Jochen Kenndoff, Hamburg (DE)

(73) Assignee: Dr. Kenndoff GmbH & Co. KG, Hamburg (DE)

( * ) Notice: Subject to any disclaimer, the term of this patent is extended or adjusted under 35 U.S.C. 154(b) by 325 days.

(21) Appl. No.: 14/342,745

(22) PCT Filed: Sep. 4, 2012

(86) PCT No.: PCT/EP2012/003690
§ 371 (c)(1),
(2), (4) Date: Apr. 4, 2014

(87) PCT Pub. No.: WO2013/034277
PCT Pub. Date: Mar. 14, 2013

(65) Prior Publication Data
US 2014/0296764 A1    Oct. 2, 2014

(30) Foreign Application Priority Data

Sep. 6, 2011 (DE) .................. 10 2011 112 433

(51) Int. Cl.
| | | |
|---|---|---|
| *A61D 9/00* | (2006.01) | |
| *A61L 15/58* | (2006.01) | |
| *A61L 15/60* | (2006.01) | |
| *A61F 13/02* | (2006.01) | |
| *A61F 13/00* | (2006.01) | |

(52) U.S. Cl.
CPC ............ *A61D 9/00* (2013.01); *A61F 13/0223* (2013.01); *A61L 15/58* (2013.01); *A61L 15/60* (2013.01); *A61F 2013/00131* (2013.01); *A61F 2013/00336* (2013.01)

(58) Field of Classification Search
CPC . A61D 9/00; A61F 13/00; A61F 13/02; A61F 13/0203; A61F 13/0223; A61F 2013/00089; A61F 2013/00314; A61F 2013/00323; A61F 2013/00336;
(Continued)

(56) References Cited

U.S. PATENT DOCUMENTS 4,373,519 A * 2/1983 Errede ............... A61F 13/00046
128/DIG. 21
5,844,016 A    12/1998 Sawhney et al.
(Continued)

FOREIGN PATENT DOCUMENTS

| CA | 2539148 A1 | 9/2006 |
|---|---|---|
| DE | 29611414 U1 | 9/1996 |

(Continued)

OTHER PUBLICATIONS

English Translation of the International Preliminary Report on Patentability dated Mar. 20, 2014 in corresponding International Patent Application No. PCT/EP2012/003690, filed Sep. 4, 2012.

*Primary Examiner* — Keri J Nelson
(74) *Attorney, Agent, or Firm* — Rankin, Hill & Clark LLP

(57) ABSTRACT

The invention relates to the use of a semi-occlusive flexible flat wound dressing having a wound contacting layer consisting of an elastomer or a thermoplastic elastomer component in which hydrophilic polymers are embedded, for treating contaminated wounds in animals, in particular in the region of the body limbs.

7 Claims, 1 Drawing Sheet

(58) Field of Classification Search
CPC .......... A61L 15/00; A61L 15/16; A61L 15/44; A61L 15/58; A61L 15/60
USPC .............................................. 602/41–43, 48
See application file for complete search history.

(56) References Cited

U.S. PATENT DOCUMENTS

| | | | |
|---|---|---|---|
| 6,191,216 | B1 | 2/2001 | Ganster et al. |
| 6,458,391 | B1 * | 10/2002 | Reusser ................. A61K 36/61 424/725 |
| 7,696,400 | B2 * | 4/2010 | Sigurjonsson .......... A61F 13/02 602/41 |
| 7,765,647 | B2 | 8/2010 | Smith et al. |
| 2002/0156411 | A1 | 10/2002 | Ahrens et al. |
| 2002/0160037 | A1 | 10/2002 | Ahrens et al. |
| 2004/0087884 | A1 | 5/2004 | Haddock et al. |
| 2006/0041211 | A1 * | 2/2006 | Hawkinson .............. A61D 9/00 602/41 |
| 2009/0216168 | A1 | 8/2009 | Eckstein |
| 2010/0106107 | A1 | 4/2010 | Nash et al. |
| 2011/0021964 | A1 * | 1/2011 | Larsen ................ A61L 26/0066 602/47 |
| 2011/0184327 | A1 | 7/2011 | Cameron et al. |

FOREIGN PATENT DOCUMENTS

| | | |
|---|---|---|
| DE | 29611414 U1 | 10/1996 |
| DE | 102009057267 A1 | 6/2011 |
| EP | 1190722 A2 | 3/2002 |
| EP | 1190723 A2 | 3/2002 |
| EP | 1695721 A1 | 8/2006 |

* cited by examiner

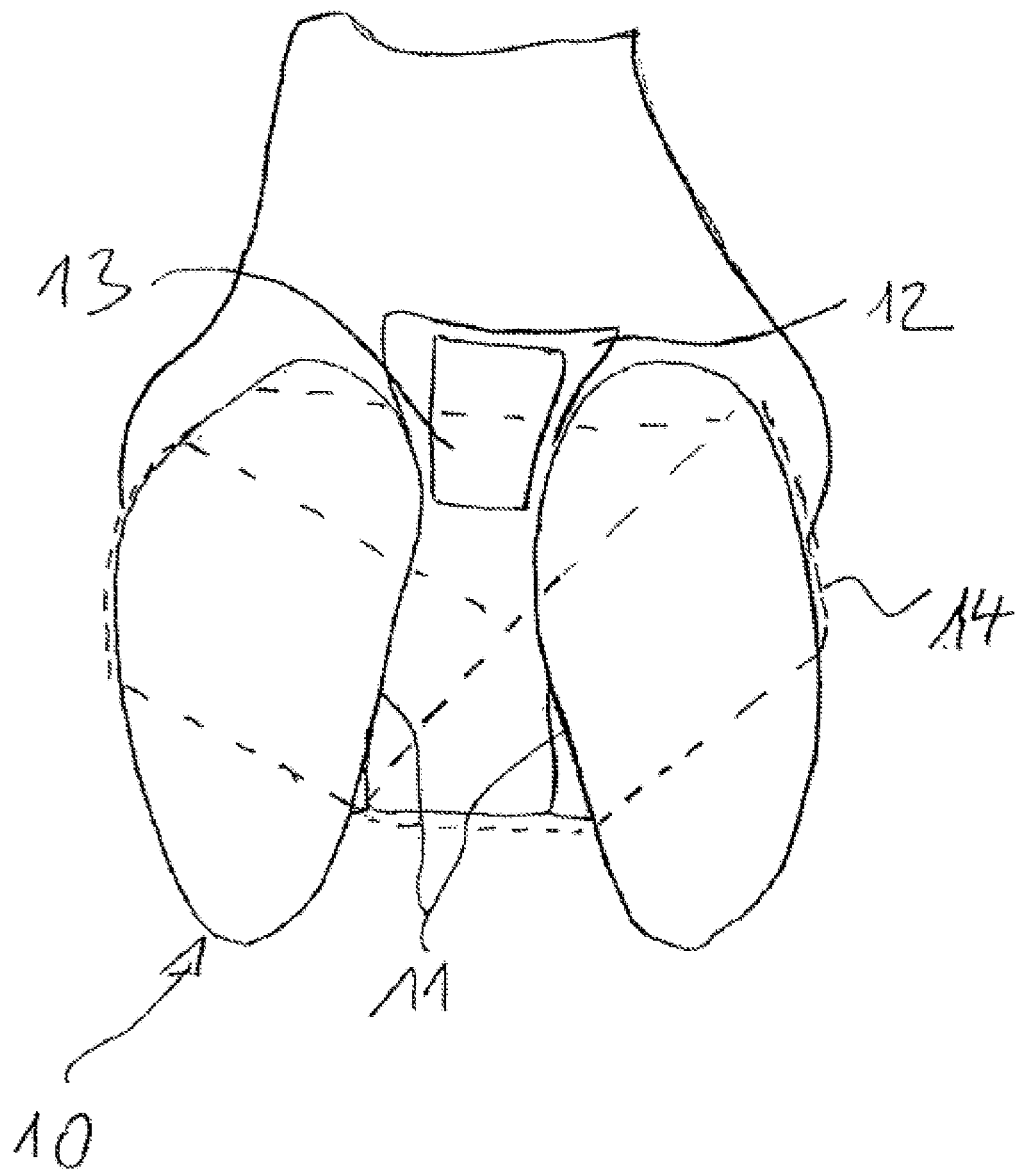

USE OF A SEMI-OCCLUSIVE FLEXIBLE FLAT WOUND DRESSING FOR TREATING WOUNDS IN ANIMALS

The invention relates to the use of a special flat would dressing for treating in particular contaminated wounds in animals. The wound dressing comprises a wound contact layer that consists in particular of polyurethane, silicone or a hydrocolloidal matrix and in which hydrophilic polymers are embedded.

The use of semi-occlusive bandages for treating wounds in animals, in particular horses, is known (see Stashak et. al. in Clinical Techniques in Equine Practice). The described and known principle of such bandages is to create a moist wound atmosphere that favors the repair phase of the wound healing. The bandages are designed in such a manner that excess liquid can evaporate through them to the outside but at the same time a dehydration of the wound is avoided.

It is described in this publication that heavily contaminated or infected wounds should be covered with an adhesive bandage until sufficient granulation tissue has developed. The use of a semi-occlusive bandage is suggested for the then following repair phase.

A special case is constituted, e.g., in the framework of Mortellaro's disease in cows. These wounds are located in the hoof area and are therefore as a rule dirty to a high degree and usually coated with inflammatory products. The sick time itself is relatively long, even given a favorable course, can result in lameness and in high losses of up to EUR 100,00 per sick animal.

The known and authorized treatment methods are based on genuine drugs, e.g., drugs containing antibiotics that are sprayed on (CTC spray or also called blue spray) with chlorotetracycline as active substance. There is the danger here for the user who has to work with them frequently or professionally of inhaling the spray mist containing antibiotics and thus developing resistances to the active substance class. Furthermore, the conditions to be observed after use (the animal should stand at least 1 hour on dry soil are unrealistic since the animals can as a rule only be discharged into their normal stall environment, that is moist in the area of the hooves.

Another treatment method is based on salicyl-containing formulations (e.g., Novaderma), that are applied as a rule with a bandage. Here, usually several successive applications are required since otherwise there is no sufficient keratolytic and antibacterial effectiveness. Furthermore, this treatment method has the problem of a waiting time for the production of milk of one day after the removal of the dressing.

Hoof baths using aggressive solutions such as, e.g., formalin solution, copper sulfate solution or chlorine-containing solutions, e.g., weakly concentrated perchloric acid solution are common, in order to name only a few examples. They are frequently not effective until in concentrations that are no longer admissible for being used.

As an alternative or a supplement, antibiotic foot baths are known.

Even the parenteral administration of antibiotics, e.g., Cefquinom, is known and described as effective. However, there is also a waiting time of 1 day after the discontinuation in the case of milk and 7 days in the case of meat to be observed.

The use of a special salve in combination with a pretreatment with blue spray is known from DE 10 2009 057 267. It is explained in the descriptions for use of the associated sales product (Mortekill) that the wound region is to be set on fire before the salve is applied.

Furthermore, freezing sprays for the treatment are also discussed and tried in practice.

However, singing and freezing result in surface burn wounds and freezing wounds similar to burn wounds that as a rule later result in distinctly larger lesions.

Most of the cited methods also have the problem that the application of solutions or salves is only effective for a limited time (namely, as long as the salve or the solution can act on the wound before it is washed off or separated by the contact of the hoof with the environment. Therefore, a bandage is also frequently put on in order to hold the agents longer on the diseased skin. However, the usually used cohesive or non-cohesive fabric bandages are permeable for the excrement from the stall and become full with it with the passage of time so that the treated region is nevertheless exposed to a contamination from the outside. This has the result that a treatment must then be repeated 2 or 3 times if necessary.

Finally, non-permeable bandages for the treatment of hoof for diseases in cattle are also known from DE 29611414U1 that consist of a paste containing in particular bitumen. However, it is to be assumed that occlusive conditions are adjusted with such a bandage that further a wound healing only to a limited extent. Occlusive conditions are basically less suitable since the germs demonstrated in these wounds are usually anaerobic bacterial strains.

The invention has the problem of offering a possibility of treatment that avoids the previously described disadvantages of the currently existing treatment forms.

This problem is solved in accordance with claim 1.

The invention provides treating the cited problematic wounds such as are known in particular as Mortellaro's disease in cows or, e.g. scurf in horses with a special semi-occlusive wound dressing that comprises a wound contact layer consisting of an elastomeric or thermoplastically elastomeric component in which the hydrophilic polymers are embedded.

An especially suitable wound dressing is described further below in example 1.

It was surprisingly determined that wounds in different stages (acutely active, chronically active, in the process of healing, inactive, etc.) can be treated equally well with the wound dressing in accordance with the invention. The treatment of the wound in accordance with the invention by covering with a special wound dressing furthers the formation of granulation tissue in the case of deeper defects as well as the subsequent epitheliazation phase, which was not to be expected in any case considering the problems described in particular in combination with the treatment of Mortellaro's disease.

It is especially surprising that the use in accordance with the invention of the wound dressing without the addition of medicaments is possible (wetness, dirt) and leads to rapid healing successes without problems, as explained further, even under the customary conditions of maintaining the animals, especially the cattle. As a rule it is sufficient to cover the wound in a flat manner with the wound dressing used in accordance with the invention and to secure it then with another bandage on the hoof in such a manner that that the contact of the wound dressing with the wound surface or the wound secretion is ensured and is held for several days in this position by a fixing. At the same time the fixing presses the wound dressing onto the still intact skin so that dirt can no longer subsequently flow under the wound dressing. The semi-occlusive property of the material prevents dirt and bacteria from being able to penetrate through the storage device into the wound region yet the covered region can still breathe. In this manner the wound region cleaned by the cleaning process of the body itself cannot be re-contaminated from the outside and the animal organism can build up an intact skin barrier without being disturbed. It is also ensured in this manner than no anaerobic environment could arise in which some of the noxious germs could thrive especially well. Also, the entire problem resulting from the use of antibiotics such as the developing of resistances to antibiotics or the endangering of the users is avoided as a result in an elegant manner.

The disadvantages of known treatments can be eliminated in a simple manner with the invention.

The customarily heavily contaminated and possibly inflammatory wounds can be effectively protected against further contamination from the outside by using a semi-occlusive wound dressing that makes contact with the wound. The wound dressing forms a type of scab replacement that protects the wound from further contamination from the outside. A hard scab that may form (in the case of scurf) is softened and a tearing open of any hard scab that may have formed is prevented.

Since no anaerobic conditions are present under the dressing, a survival of the especially critical anaerobic bacterial strains becomes difficult or is prevented. The animal organism is given the possibility to create and maintain an environment on the wound that promotes healing. After a mechanical pre-cleaning by the user the self-cleaning of the wound region by the organism of the animal from germs and contaminations that are still or already in the wound can begin and the forming of an intact skin barrier can take place.

It surprisingly turned out that a single treatment is sufficient.

A quite important advantage of the invention is the fact that for the treatment of, e.g., Mortellaro's disease no drugs, in particular prescription drugs, are necessary. In particular, not having to use the customarily used antibiotics prevents the formation of resistances in the animal and the user. Another important advantage is the fact that the treatment has no waiting time, in other words, the owner of the animal can use the animal without interruption and it is also not required that the animal has to be maintained after and during the treatment under unrealistic conditions.

Practically speaking, it is quite significant that the bandage does not have to be prescribed by a veterinarian as an authorized drug and can therefore be directly ordered and used without problems by pertinent professional groups such as, e.g., the cattle raisers or the farmer himself.

As explained above, the wound contact layer consists of a moisture-permeable matrix in particular, e.g., of hydrophilic polyurethane. Hydrophilic polymers area embedded in it that can bond liquid such as, e.g., pectin, gelatin, carboxymethylcellulose or superabsorbers.

The wound contact layer of the wound dressing can be foamed or not foamed, adhesive or non-adhesive.

It is possible to apply the dressing with traction or also without traction. All that is important is that the contact of the wound dressing with the wound surface or the wound secretion is ensured so that the desired moist wound healing climate can develop and a contamination from the outside under the bandage cannot occur.

Furthermore, it is important that the material is formed in such a manner that no dirt and no bacteria can pass through the bandage into the wound area.

The wound dressing used in accordance with the invention is preferably a composite of a wound contact layer with a flat carrier arranged on one side on it. The wound contact layer comprises a plastic and/or elastic deformability that ensures that the wound contact layer can adapt to the given contour when the wound dressing is applied. Ideally, a thickness is selected that can additionally cushion the wound region is a sufficient manner. Also, the carrier of the wound contact layer can have cushioning properties (e.g., a foam that relieves pressure) and the wound contact layer itself can be constructed to be only very thin. The cushioning is not obligatorily necessary, however. In any case the carrier surface should be such that the material can reduce the friction between the wound region and the hoof horn so that even during use an additional friction is avoided especially in the intermediate hoof gap.

The thickness and deformability of the wound contact layer and/or of the carrier are preferably selected for the wound dressing used in accordance with the invention in such a manner that in spite of local expansion of the bandage a sufficiently thick layer cushions the wound region.

The thickness of the wound contact layer used and/or of the carrier is preferably 50-3000 µm, preferably 150-2000 µm and especially preferably 250-1000 µm. The deformability of the wound contact layer should preferably be such that the carrier of a film adhered flat on steel can be shifted by at least 100% of its height, preferably more than 300% and especially preferably more than 500% from the edge to the middle of the plaster. This can be seen most clearly in the case of a self-adhering product that is adhered on a steel plate and is not separated from the steel plate during the indicated shifting. In other words, the carrier can be shifted back in the case of a 1 mm thick adhesive layer in this embodiment by at least 1 mm, preferably by >3 mm, especially preferably by >5 mm.

Furthermore, it is preferably provided that the wound contact area is provided with an elasticity that is especially preferably adjusted in such a manner that after the release of the carrier in the above-indicated investigation method the adhesive layer deforms back into its original shape.

It can occur in the case of too little deformability or elasticity that the wound contact layer has no contact with the wound surface in spite of a fixing bandage placed from the outside. The consequence is that in this case no healing-promoting, moist wound environment can develop on the wound surface and contaminants can flow from the outside under the bandage.

In addition, the material should reduce the friction between the wound region and the hoof horn so that even when used in particular in the intermediate horn gap an additional friction is avoided. Ideally, the wound contact layer or the carrier film is designed in such a manner that a cushioning of the wound region is additionally given.

Thickness, elasticity and optionally plastic deformability of the wound contact layer are therefore advantageously coordinated with each other in such a manner that that frictional forces acting during the standing and walking of the animal can be compensated.

Furthermore, it is especially advantageous if not only the wound contact layer but also the wound dressing are constructed altogether in such a manner that that they satisfy these requirements.

In the following in particular other details of the wound contact layer are to be discussed.

Wound contact layers that are preferred in the scope of the invention can be non-adhesive or have adhesive forces on steel >0.5 N/cm, preferably >0.7 N/cm, and especially preferably >1 N/cm. The indicated adhesive forces refer to measurements of adhesive forces on standardized steel plates. This is a standard method known to the person skilled in the art.

Furthermore, the wound contact layer used in accordance with the invention should be sufficiently permeable to water vapor in order that the skin located underneath it does not become macerated, in particular after a rather long wearing time. Maceration is not desired since it makes the skin distinctly more susceptible to the attack of germs.

Wound contact layers are suitable that are permeable to water vapor, can contain pores or are worked into the moisture-absorbing filling substances.

Therefore, in particular polyurethane adhesive layers, silicone adhesive layers or hydrocolloidal adhesive layers are preferred as wound contact layers that have, together with the carrier, a permeability to water vapor of at least 300 g/m$^2$ in 24 h, preferably 500 g/m$^2$ in 24 h or more and/or absorb at least these amounts of moisture from the skin surface within this time period and can bind it in the wound contact layer and/or in the carrier.

It is provided in accordance with the invention that the wound contact layer does not interfere or stick but rather it preserves a moisture environment on the wound surface comparable to that under a natural scab. Thus, the wound contact layer does not adhere in the wound bed and therefore promotes an accelerated healing of the wound.

The wound contact layer should furthermore have the lowest possible potential for sensibilization.

The permeability of the wound dressing to oxygen is of great importance in order that the skin that is covered for several days can continue to breathe through the bandage and that anaerobic bacteria cannot grow. Otherwise, the skin could become irritated or anaerobic bacteria could multiply without hindrance. This contributes to the fact that the wound dressing can be left more days on the wound, which for its part improves the protection of the wound region and supports the healing-promoting environment.

It is also significant that the wound contact layer used in accordance with the invention can absorb wound secretion under pressure and does not release it again. This can be achieved by mixing superabsorber particles or other suitable hydrophilic polymers such as are known, e.g., from the manufacture of diapers to the adhesive layer. Suitable particles are commercially available, e.g., under the designation FAVOR T 5233.

The wound dressings used in accordance with the invention can be optimized by advantageous embodiments of the carrier.

Basically suitable carriers can all consist of all flexible, flat materials that allow a flat cut and have, e.g., the properties known from the area of plaster- or bandage technology. Carriers that can be used here are, for example, woven fabrics, knit fabrics, fleeces and films as well as combinations of these materials. Suitable films are, e.g., polyethylene films, polyurethane film, copolyester films, polyamide films and co-extruded films. Suitable fleeces are, e.g., cellulose acetates, polyester fleeces or polyamide fleeces. The above data is a non-conclusive enumeration of a few examples. Of course, a number of other materials known to the person skilled in the art are suitable as carriers for production.

According to an advantageous embodiment a carrier is used that is constructed to be flatly expandable. The expansion should be selected in such a manner that that the carrier can expand with the wound contact layer to at least >50%, preferably >100% of its extension in this direction. It is especially preferred if the carrier and the wound contact layer can expand substantially synchronously.

The expansion of the carrier can take place by stretching as well as by elastic expansion with all percentage conditions located between stretching and elasticity.

It is preferably provided that the carrier can expand longitudinally and transversely to the surface of use. Here too, the expansion can again be due to elasticity or to stretching.

The surface of the carrier facing away from the wound contact layer should be of such a nature that it reduces the friction between the wound contact layer and the horn, in particular in the intermediate hoof gap. Therefore, macroscopically smooth films such as, e.g., polyurethane films, polyethylene or polyester films or compounds of several different materials that are visibly smooth, germ-tight and flexible are preferred as carriers. Less suitable but also possible are, for this reason, more heavily structured surfaces such as, e.g., knit fabrics, woven fabrics or fleeces, even if they were rendered hydrophobic.

The carrier is itself or in combination with the wound contact layer germ-tight and remains so even during the expansion or stretching.

As a rule, it is required that the wound dressing is fixed with an additional bandage and is pressed, if necessary, on the wound region.

The fixing ideally takes place by elastic, cohesive binding, elastic "shoes" that can be drawn over or also products such as, e.g., cowslipper, designed for covering and fixing in the region of the hoof. Even non-elastic bindings can be used.

An especially preferred wound dressing comprises a carrier coated with a self-adhesive polymer matrix as wound contact layer. Qualities such as are sufficiently described in patent EP 0 897 406 are considered as example of an embodiment relevant for the application. The degree of moistening preferred for the application in accordance with the invention is characterized as the characteristic isocyanate number as described in patent EP 0 897 406, and is preferably in the range of 41-47 without, however, wishing to exclude the characteristic number ranges cited in the previously cited patent. Preferably 5-20% of a filler relative to the amount of polyol used are added to the polymeric matrix described in this patent which filler is capable of absorbing and binding watery liquids without, however, wishing to exclude the amounts and qualities of filler cited in the previously cited patent and in patent EP 0 665 856. The adhesive layer characterized in this manner is covered with a highly flexible polyurethane film permeable to water vapor and oxygen without, however, wishing to exclude the alternative wound dressing cited in the previously cited patents. The product is covered with commercially available separating- or protective papers or separating- or protective films that are familiar to the person skilled in the art for self-adhesive or non-adhesive products and that have to be removed before use in order to protect the wound contact side up to the time of use.

The product for the usage in accordance with the invention can be stamped or cut out from flat material as individual plasters or be used cut off from a roll. The latter instance makes a piece of plaster possible that is adapted to the size of the wound by cutting off.

However, plasters can also be cast individually. Methods are cited by way of example that are described in the patent application EP 1 695 721.

It is surprising for the person skilled in the art that the wound dressing described in the scope of the invention can heal surface wounds without medicinal treatment under the extremely hygienic conditions.

The method and the film in accordance with the invention can be used for all animals suffering from such surface wounds such as, e.g., cows, horses, etc. that suffer from an acute, inactive or chronic form of, e.g., Mortellaro-like or scurf-like lesions.

The invention is explained in detail in the following using an example for a suitable wound dressing and a FIGURE that shows in a rough schematic manner a hoof with placed wound dressing, and using test results.

EXAMPLE FOR A SUITABLE WOULD DRESSING

A suitable wound dressing is built up from an approximately 40 μm thick, highly flexible polyurethane film that is permeable to water vapor and oxygen and is germ-tight (Applica, Smith & Nephew) as carrier, that is coated with a self-adhering 300 μm thick, highly flexible adhesive layer of polyurethane as wound contact layer.

The adhesive layer was produced in that 100 wt % polyol (Levagel VP KA 8732; OH number 35) is homogenized with 12 wt % superabsorber (Favor T 5233), 0.1 wt % catalyst (Coscat 83) and 0.8 wt % vitamin E (Irganox E 201) in a 1-1 apparatus 2 h at room temperature. Then, 6.6 wt % cross-linking agent (Desmodur E 305, NCO content 12.2%) was added to 100 wt % of this mixture and this mixture intensively mixed with a glass rod for 1 minute.

This mixture is then poured onto a commercially available, siliconized separating paper, covered with the polyurethane foil serving as carrier and distributed flat with the aid of a doctor blade so that the composite has a thickness of approximately 300 μm and is then hardened in a drying oven for 18 minutes at 80° C. A transparent wound dressing is produced.

Strips with a width of, e.g., 5 cm wide are cut out from the flat structure produced. The width can naturally vary. A strip with the width of 5 cm is well-suited, for example, for covering the usual size of lesions occurring in the area of the transition from the coronet edge to the bulb, of the hock bend and of the intermediate hoof gap.

The length of the strip should be selected to be approximately 16 cm so that the area of the transition from the coronet edge to the bulb, of the hock bend and of the intermediate hoof gap can be covered with the strip. If the lesion is only in the area of the transition from the coronet edge to the bulb or of the hock bend a round or angular shape with 5 by 5 cm is also sufficient. The separating paper is drawn off from the wound contact layer and the wound dressing placed without tension onto the wound region. An oblong strip of 5×16 cm is placed into the intermediate hoof gap in such a manner that material for covering projects in the area of the hock bend or in the area of the coronet edge and makes contact with the skin surface or wound surface in the intermediate hoof gap. The supernatant should be capable of covering seasons in the region of the hock bend or in the region of the coronet edge. The lesion only in the region of the hock bend or only in the region of the transition from the coronet edge to the bulb can be covered with a wound dressing with a size of 5×5 cm. In any case it must be ensured that the wound dressing covers all lesions exposed during the cleaning. If necessary, several bandages can be placed in an overlapping manner so that at least all exposed lesions are covered by the wound dressing. The fixing takes place optionally after an additional placing of a cushion in the area of the hock bend in order to ensure the contact of the wound dressing with a wound surface with the aid of a cohesive bandage (e.g., Eurofarm adhesive bandages).

The wound dressing can now be placed in fixed in such a manner that it remains about 10 days on the hoof. Held by the bandage, it remains in position and does not separate off.

If the skin regions of the hoof have a lesion, then the wound dressing is put on exactly as described above. Here, the wound dressing assumes the function of a scab and protects the wound against contamination and germs. Excess wound liquid is slowly absorbed by the wound bandage. For removal, the cohesive bandage is simply cut open and removed together with the wound dressing.

The single FIGURE shows in a roughly schematic manner a hoof 10 with intermediate hoof gap 11 in a top view. A non-recognizable wound is present in the region of the intermediate hoof gap 11 which wound is covered in accordance with the above example with a wound dressing 12. In order to increase the contact of the wound dressing, a cushion 13 is arranged on it and the wound dressing 12 and the cushion 13 are then fixed with an elastic bandage 14 that is wound several times around the hoof.

Reference Tests:

In order to document the effectiveness of the invention several sick animals were treated with different products. The results after 8 days of treatment time are collated in the following table:

TABLE

| Product | Cut | Animal | Wound position | Status at start of treatment | Success after 8 days of treatment |
|---------|-----|--------|----------------|------------------------------|-----------------------------------|
| Example | 5 × 16 cm | 648 | HL b | DD cranially active and inactive, L | Limax healed |
| Example | 5 × 16 cm | 656 | HR b | DD active on L | DD healed; L still present |
| Example | 5 × 16 cm | 681 | HR b | DD active on L | DD, L healed |
| Example | 5 × 16 cm | 760 | HR b | DD active | healing |
| Example | 5 × 16 cm | 760 | HR c | DD active | Healing |
| Example | 5 × 16 cm | 786 | VR c | DD active | Healed |
| Example | 5 × 16 cm | 33936 | HR b | DD active | Healing |
| Example | 5 × 16 cm | 82391 | HR a/b/c | DD active | Healing |
| Example | 5 × 16 cm | 82392 | HL c | DD active | Healing |

TABLE-continued

| Product | Cut | Animal | Wound position | Status at start of treatment | Success after 8 days of treatment |
|---|---|---|---|---|---|
| Example variant varies: thin, adhesive, foamed, elevated amount of superabsorber | 5 × 6 cm | 773 | HR c | DD active | Healing |
| Gel-forming hydrocolloidal bandage | 5 × 5 cm | 802 | HR c | DD active | Healing |
| Example variant varies: thick, adhesive, non-foamed, greatly elevated | 5 × 6 cm | 773 | VL sole | SWG active | derma raised to normal level = filling out of defect |
| Hydrophobically coated compress | 5 × 5 cm | 766 | HL a/dorsal | DD active | Not healing |
| Hydrogel | 5 × 5 cm | 772 | HL c | DD fully active | Not healing |
| Compress containing superabsorber | 5 × 5 cm | 772 | HR c | DD active | Not healing |
| Fatty gauze | 5 × 5 cm | 786 | HL c | DD active | active |
| Alginate | 5 × 5 cm | 794 | HR c | DD active | Active |
| PU foam | 5 × 5 cm | 802 | HL c | DD active | Active |
| Silicone-foam bandage | 5 × 5 cm | 33936 | HL a | DD active | Not healing |
| PU foam | 5 × 5 cm | 33936 | HR c | DD active | Active |

DD = digital dermatitis;
L = Limax;
SWG = sole wall ulcer;
HL, HR, VL, VR = rear left, rear right, front left, front right;
a = transition coronet edge to the bulb;
b = ZKS (intermediate hoof gap);
c = hock bend;
d = hoof sole It can be recognized that the use of the wound dressing (example) described in the example led for all treated animals (648-82392) to a successful healing. The exemplary variants and a gel-forming hydrocolloidal bandage also displayed a good effect.

On the other hand, the bandages used for the animals 766 to 33936 for ineffective. No healing was able to be observed here after 8 days.

The invention claimed is:

1. A method for the treatment of a wound on a body limb of an animal, the method comprising:
   providing a semi-occlusive in its entirety, flexible, flat wound dressing, said wound dressing being a composite consisting of
   (i) a self-adhesive wound contact layer formed by mixing hydrophilic polymers with precursors that polymerize into an elastomeric or thermoplastically elastomeric matrix in which the hydrophilic polymers are embedded, and
   (ii) a flat carrier arranged on one side of the wound contact layer; and
   fixing the wound dressing on the body limb of the animal with the wound contact layer in contact with the wound.

2. The method according to claim 1, wherein the animal is a cow and the wound being treated is Mortellaro's disease.

3. The method according to claim 1, wherein the animal is a horse and the wound being treated is scurf.

4. The method according to claim 1, wherein the wound contact layer comprises a polyurethane, a silicone or a hydrocolloidal matrix.

5. The method according to claim 1, wherein the embedded, hydrophilic polymers are hydrophilic, liquid-binding particles.

6. The method according to claim 5, wherein the hydrophilic, liquid-binding particles are selected from the group consisting of pectin, gelatin, carboxymethylcellulose and superabsorbers.

7. The method according to claim 1, wherein the wound dressing comprises a breathable plastic film as the flat carrier.

* * * * *